US012767918B2

(12) United States Patent
Wang et al.

(10) Patent No.: US 12,767,918 B2
(45) Date of Patent: Oct. 20, 2026

(54) MICROFLUIDIC ELECTROPORATION DEVICE

(71) Applicant: ORIENTAL SYSTEM TECHNOLOGY INC., Hsin-Chu (TW)

(72) Inventors: Chein-Hsun Wang, Hsin-Chu (TW); Yun-Hsiang Chen, Taipei City (TW); Jyh-Yih Leu, New Taipei City (TW); Wen-Chie Huang, Hualien County (TW); Chin-Hsiang Chang, New Taipei City (TW); Jenping Ku, Hsinchu County (TW); Ming-Tsung Yang, Hsinchu County (TW)

(73) Assignee: ORIENTAL SYSTEM TECHNOLOGY INC., Hsin-Chu (TW)

(*) Notice: Subject to any disclaimer, the term of this patent is extended or adjusted under 35 U.S.C. 154(b) by 641 days.

(21) Appl. No.: 18/362,312

(22) Filed: Jul. 31, 2023

(65) Prior Publication Data

US 2025/0043227 A1 Feb. 6, 2025

(51) Int. Cl.
*C12M 1/42* (2006.01)
*C12M 1/00* (2006.01)
(Continued)

(52) U.S. Cl.
CPC ............ *C12M 35/02* (2013.01); *C12M 23/16* (2013.01); *C12M 23/40* (2013.01); *C12M 25/06* (2013.01)

(58) Field of Classification Search
None
See application file for complete search history.

(56) References Cited

U.S. PATENT DOCUMENTS

2016/0237397 A1 8/2016 Guia et al.
2022/0126292 A1* 4/2022 Espinosa ........... B01L 3/502707

FOREIGN PATENT DOCUMENTS

CN 112094742 A 12/2020
CN 113832033 A 12/2021
(Continued)

OTHER PUBLICATIONS

Office Action dated Apr. 11, 2024 of the corresponding Taiwan patent application No. 112132181.

*Primary Examiner* — William H. Beisner
*Assistant Examiner* — Julius Francis Yoh
(74) *Attorney, Agent, or Firm* — MUNCY, GEISSLER, OLDS & LOWE, P.C.

(57) ABSTRACT

A microfluidic EP device for exogenous molecules transfection is disclosed that has high speed, high viability, and efficiency for collection of cells after EP. The microfluidic EP device has an EP chamber assembly, an adaptor, a pop up device, a syringe pump assembly, an EP controller, and a system controller. The EP chamber assembly has a MEMS nano channel plate, a MEMS cap, a cell cavity plate, and a cell cavity plate holder. The EP chamber assembly is connected to the pop up device through the adaptor. The pop up device may be an ultrasound vibrator or a motorized rotator. The MEMS cap has inlets/outlets for inputting/outputting cell solution, washing solution, transfected cells, exogenous material solution. The solution fluid is inputted/outputted by plastic tube and needle adaptor to the syringe pump assembly. All operation sequences are controlled by the system controller, which may perform batch operation continuously.

19 Claims, 10 Drawing Sheets

(51) Int. Cl.
*C12M 1/12* (2006.01)
*C12M 3/06* (2006.01)

(56) References Cited

FOREIGN PATENT DOCUMENTS

| | | | |
|---|---|---|---|
| TW | 202003833 | A | 1/2020 |
| WO | 2014144219 | A1 | 9/2014 |
| WO | 2016112349 | A1 | 7/2016 |

* cited by examiner

MICROFLUIDIC ELECTROPORATION DEVICE

BACKGROUND OF THE INVENTION

Technical Field

The present invention relates to a microfluidic electroporation device for transfection of cells, which has a pop up device and an electroporation chamber assembly made by MEMS (micro-electromechanical system) process.

Description of Related Art

Electroporation (EP) is a process to apply an electrical field across a cell membrane to achieve temporary "pore" formation on the cell membrane, and to enable the uptake of the exogenous molecules into the cytoplasm or the nucleus, thereby transfecting or transforming the cell.

In the related art, a high voltage (for example, greater than 1000V, or the electric field in the order of about several kV/cm) is needed to be applied to create temporary pore on a cell membrane. Under microfluidic conditions the electric field strength and duration must be well controlled in order to improve the viability of cells to be transfected. To increase the viability and transfection efficiency of cell, the electric field is required to be uniformly applied to each cell. By using microchannel method, the applied voltage may be controlled within 1-3 KV/cm while maintaining uniform electric field strength for EP to each cell. By keeping the distance between exogenous material to cell in several hundreds of um, the applied voltage can be reduced to tens of volts and get the same required electric field strength.

By using spatial confinement in micro scale for EP, it provides numerous benefits over related-art bulk EP, for example, rapid cargo uptake, precision dosage control and minimum cell disturbance.

Spatial confinement of EP methods includes microchannel (microfluidic) EP and microcapillary EP. The bench marks for EP are viability and efficiency, that is, the viability of transfected cells and how much percentage of cells or how many cells are transfected simultaneously.

Hence there is a need for a high speed, high efficiency, and high viability device for transfection of cells.

In view of this, the inventors have devoted themselves to the aforementioned related art, researched intensively try to solve the aforementioned problems.

SUMMARY OF THE INVENTION

One objective of the present invention is to provide a microfluidic EP device for transfection that has the features of high viability and high efficiency.

For the spatial confinement of cells to be transfected, micro cavities formed by MEMS (micro-electromechanical system) process and usage of a pop up device (for example, ultrasound vibrator or motorized rotator) are disclosed that may be used to capture cells within cavities for EP.

One embodiment of the present invention provides a microfluidic EP device includes an EP chamber assembly, an adaptor, a pop up device, an EP controller, a syringe pump assembly, and a system controller. The EP chamber assembly includes a MEMS nano channel plate, a MEMS cap, a cell cavity plate, and a cell cavity plate holder. The pop up device may be an ultrasound vibrator.

The MEMS nano channel plate may be made of silicon wafer. The MEMS nano channel plate has multiple wells mapped to the cell cavities, and each well has multiple nano channel holes for the exogeneous material solution to pass through during EP phase. The MEMS nano channel plate is attached to the MEMS cap by the conductive adhesive to bring out conductive electrode for negative terminal. The MEMS cap has an input solution buffer, an output solution buffer area, and a cell EP chamber. The input/output of the solution is done by connecting inlets/outlets of the MEMS cap with a plastic tube. On the top of the MEMS nano channel plate, the MEMS cap and the MEMS nano channel plate forms the exogenous material chamber. The inlets/outlets communicate with the exogenous material chamber for the exogenous material solution to be inputted or outputted by the syringe pump assembly. All of the inlets/outlets of the MEMS cap are connected to each syringe pump assembly through the plastic tube with the needle adaptor.

The distance between the MEMS cap and the cell cavity plate defines a narrow gap for the cell EP chamber, the distance is in a range from 100 um to 300 um. For the cell cavity plate, one cell cavity is mapped to one group of nano channel holes (with diameter between 0.5 um to 1 um) in the MEMS nano channel plate. During the EP phase, the cell cavity is connected to a positive terminal and the MEMS nano channel plate is connected to a negative terminal. The EP controller controls the voltage level, ON/OFF duration and pulse number with an electrical field strength between 1 kV/cm to 3 kV/cm during EP phase, which is triggered by the system controller.

The pop up device is used to pop up cells in the cavities, and the transfected cells are collected by inputting the washing solution and being outputted from the transfected cell outlet. When an ultrasound vibrator serves as the pop up device, the system controller controls the ultrasound amplitude, duty cycle and duration of the ultrasound vibrator.

In some embodiments, the ultrasound vibrator is made of a piezoelectric device with the material of polyvinylidene fluoride (PVDF) or lead zirconate titanate (PZT) etc., and the PZT material is more desirable. The ultrasound frequency of ultrasound vibrator is between 20 Khz to 200 Khz, and the frequency of 40 khz is more desirable.

Another embodiment of present invention of the microfluidic EP devices includes a striped-type MEMS nano channel plate, that is mapped to a striped-type cell cavity plate, to increase the cell number for transfection and still maintain the same EP parameters. The shape of each striped cavity may be a rectangular shape or a V-grooved shape that is manufactured by hot stamping.

Another embodiment of present invention of the microfluidic EP devices uses motorized rotator to replace ultrasound vibrator as the pop up device to increase the cell viability after transfection.

In some embodiment, the metal layer being coated on the top surface of the cell cavity plate may be bio-compatible material (for example, gold) with thin thickness (for example, less than 50 nm) to offer visible inspection of cells in the cavity.

In some embodiment, an air exit hole may be defined on the top surface of the MEMS cap communicating with the exogenous material chamber.

In summary, the present invention discloses a microfluidic EP device for transfection of exogenous molecules into cells with high speed, high viability, and high efficiency. The cells to be transfected are fixed in cavities of the cell cavity plate, and a low voltage pulse is applied during EP phase. By using cell cavity to capture cell in place and applying positive voltage to cell membrane, the present invention increases the viability of the cell due to uniform electric field to each cell's membrane. Meanwhile the transfected cells may be collected by the pop up device (for example, ultrasound vibration or motorized rotator) with the washing solution to be pushed out through outlet from the cell EP chamber.

Therefore, compared with the related art of microchannel EP, the present invention has the feature of high speed and may be used in mass transfection of cells with the help of the pop up device and the cell cavities to fix cells during EP phase.

BRIEF DESCRIPTION OF THE DRAWINGS

In order to further understand the techniques, means, and effects of the present invention for achieving the intended object. Please refer to the following detailed description and drawings of the present invention. The drawings are provided for reference and description only, and are not intended to limit the present invention.

DETAILED DESCRIPTION

The following are specific examples to illustrate some implementations of the present invention. A person skilled in the art may understand the advantages and effects of the present invention from the content disclosed in this specification. The present invention may be implemented or applied through other different specific embodiments, and various details in this specification may also be based on different viewpoints and applications, and various modifications and changes may be made without departing from the concept of the present invention.

The technical content and detailed description of the present invention are described below with the drawings.

Figure 1:
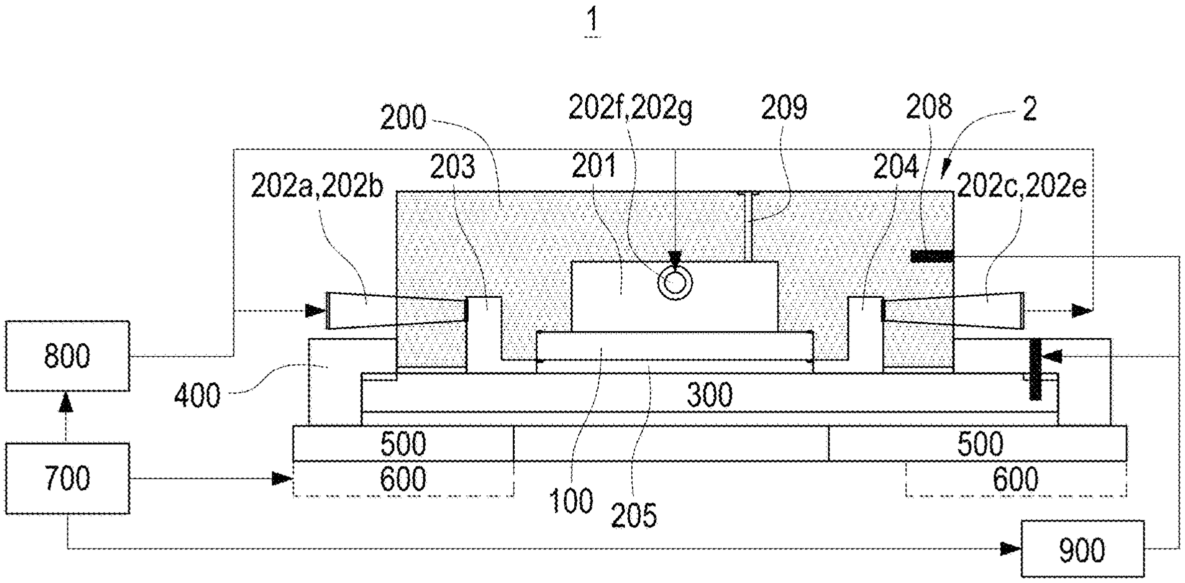
FIG. 1 is the schematic diagram of one embodiment of a microfluidic EP device of the present invention.

FIG. 1 is the schematic diagram of one embodiment of a microfluidic EP device 1 of the present invention. The microfluidic electroporation (EP) device 1 includes an EP chamber assembly 2, an adaptor 500, a cell pop up device 600, a syringe pump assembly 800 (with controller), an EP controller 900, and a system controller 700. The EP chamber assembly 2 includes a MEMS nano channel plate 100, a MEMS cap 200, a cell cavity plate 300, and a cell cavity plate holder 400. The MEMS cap 200 hosts the MEMS nano channel plate 100. The cell cavity plate 300 is attached to the cell cavity plate holder 400. Then the MEMS cap 200 is glued to cell cavity plate 300. The adaptor 500 for the EP chamber assembly 2 is attached to the cell pop up device 600 (for example, an ultrasound vibrator). The system controller 700 controls the operation of the cell pop up device 600, the EP controller 900, and the syringe pump assembly 800.

Figure 2:
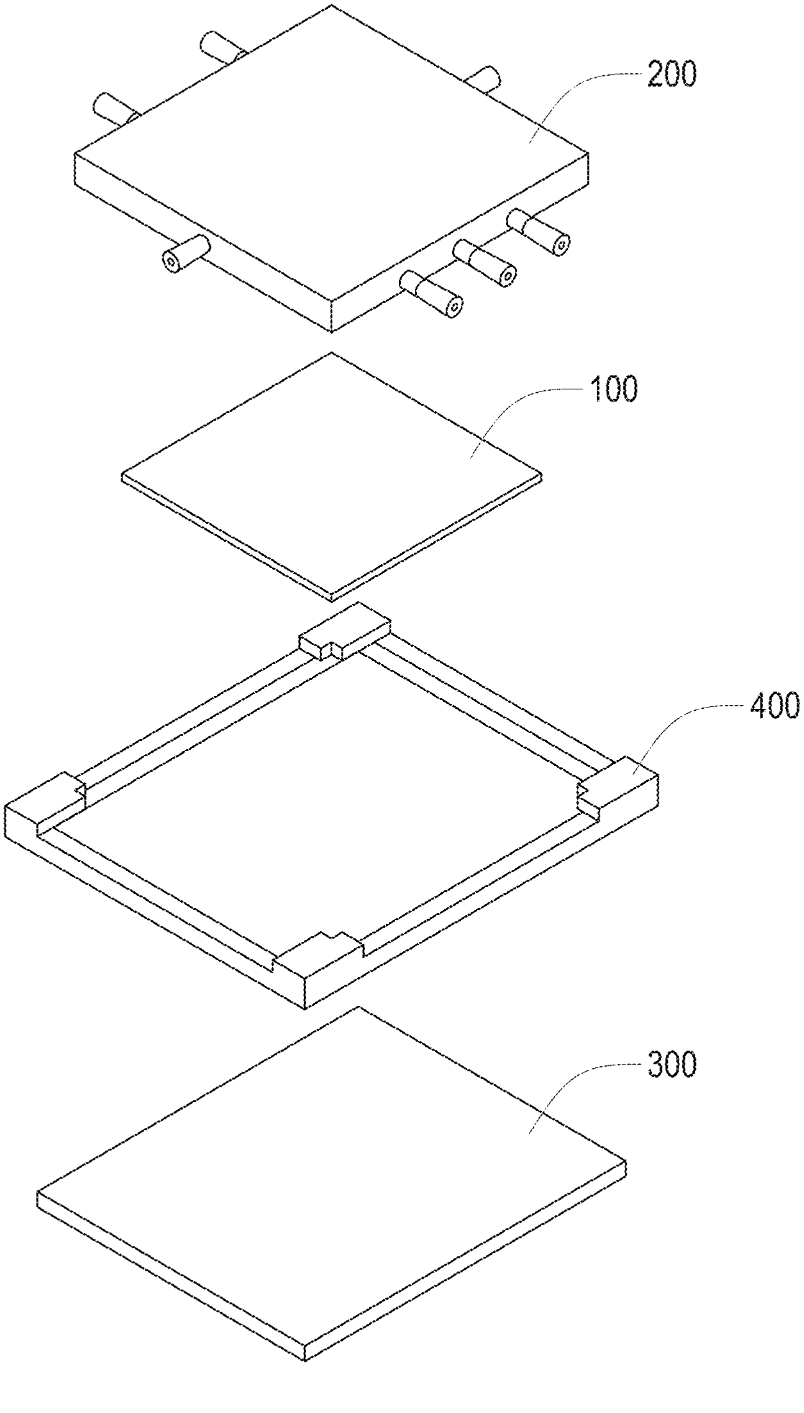
FIG. 2 is the exploded view of the EP chamber assembly of the present invention.

FIG. 2 is the exploded view of the EP chamber assembly 2 of the present invention. The EP chamber assembly 2 includes the MEMS cap 200, the MEMS nano channel plate 100, the cell cavity plate holder 400, and the cell cavity plate 300. By carefully alignment, the narrow holes for the exogenous material to pass through is mapped to the cell cavity in a vertical direction with a gap from 100 um to 300 um between exit of each nano channel hole to each cell cavity, which holds the cell to be electroporated.

Figure 3:
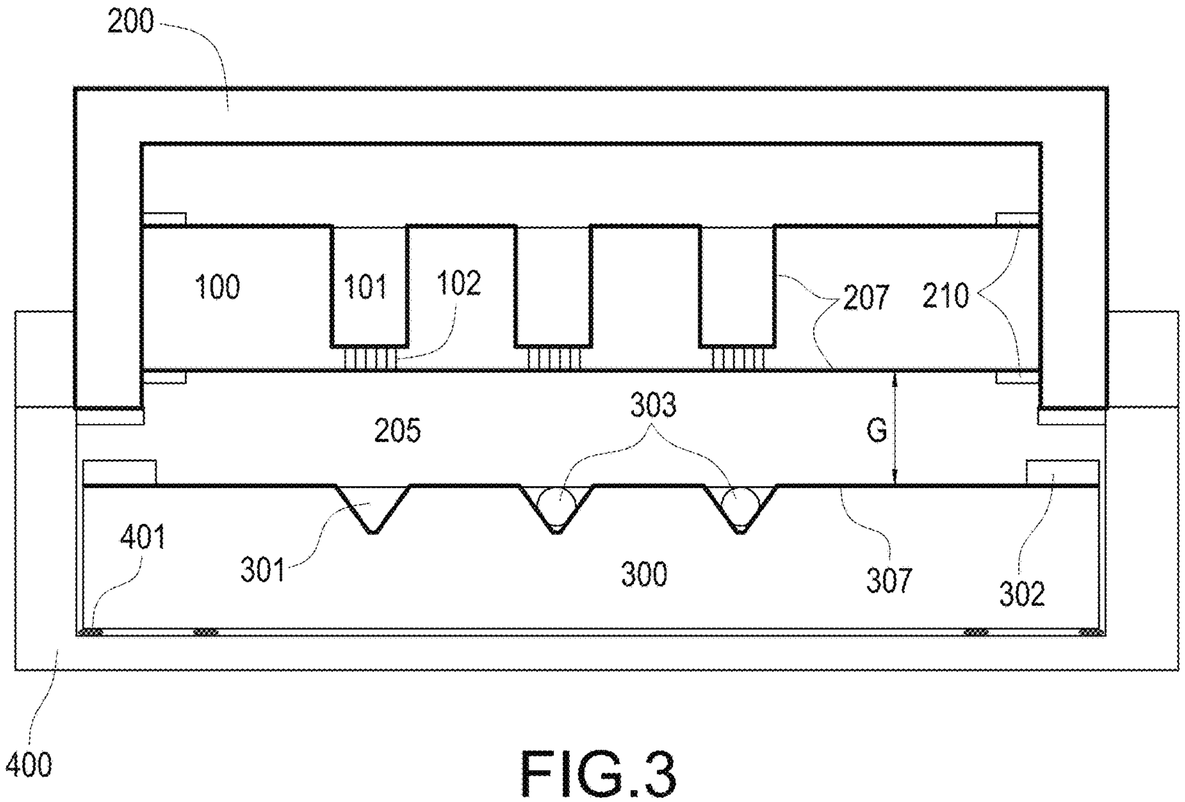
FIG. 3 is the schematic diagram of the EP chamber assembly in the microfluidic EP device of the present invention.

FIG. 3 is the schematic diagram of the EP chamber assembly 2 in the microfluidic EP device 1 of the present invention. The MEMS nano channel plate 100 has multiple wells 101. The wells are one to one mapped to the cavities 301 (cell capture cavity) with a gap G therebetween. The gap G is in a range of 100 um to 300 um, and 100 um is more desirable. Each well 101 has multiple nano channel holes 102 for the exogenous material to pass through. Each cavity in the cell cavity plate 300 may fix one cell 303 during EP phase. Multiple cells may be electroporated simultaneously. The MEMS nano channel plate 100 is coated with a metal layer 207 on double sides (upper surface and bottom surface), and the MEMS nano channel plate 100 is electrically connected to the MEMS cap 200 by a conductive adhesive 210. For bio-compatibility, the coated metal layer 207 may be a gold layer. Similarly, the top surface of cell cavity plate 300 is coated with a metal layer 307, and the metal layer 307 is connected to conductive pole 302. The cell cavity plate 300 is attached (or glued) to the cell cavity plate holder 400 by an adhesive 401. Then, the MEMS cap 200 is attached (or glued) to the cell cavity plate holder 400 to form an integrated part with a fixed gap G. Between the MEMS nano channel plate 100 and the cell cavity plate 300, a cell EP chamber is formed for the cells to flow in and flow out after EP. During EP phase, the MEMS nano channel plate 100 is connected to the negative voltage and the top surface of the cell cavity plate 300 is connected to the positive voltage through terminal 302. For the gap G at 100 um, the EP voltage is about 10 V to 30 V for an electrical field strength of 1 kV/cm to 3 KV/cm.

Figure 4A:
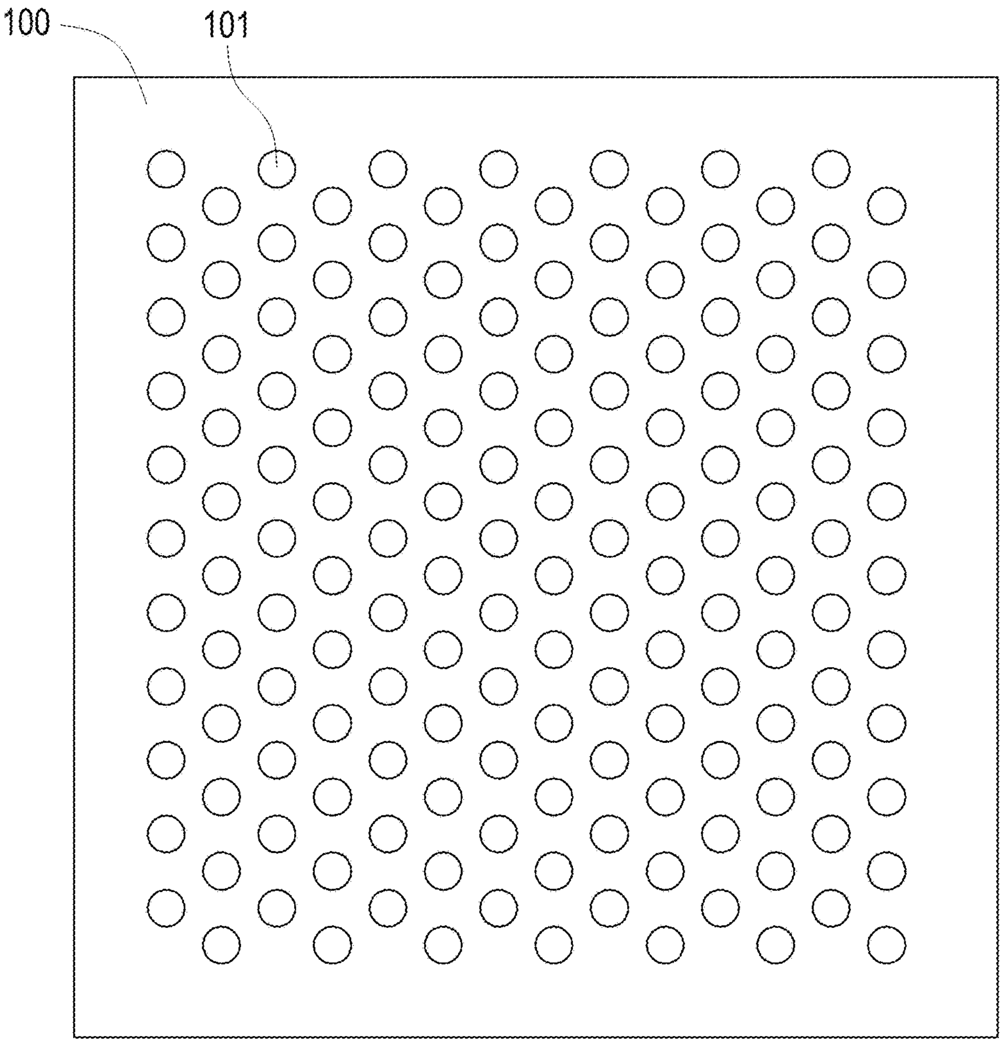
FIG. 4A is the top view of the MEMS nano channel plate.
Figure 4B:
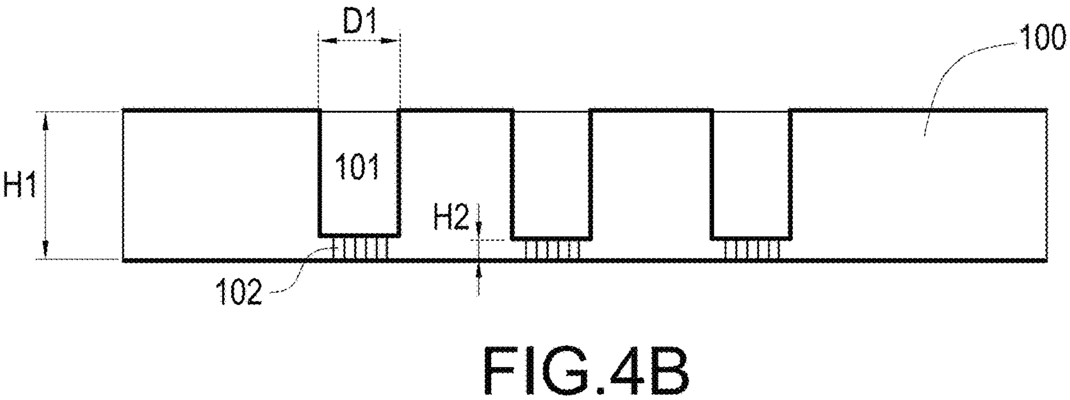
FIG. 4B is the side view of the MEMS nano channel plate.
Figure 5:
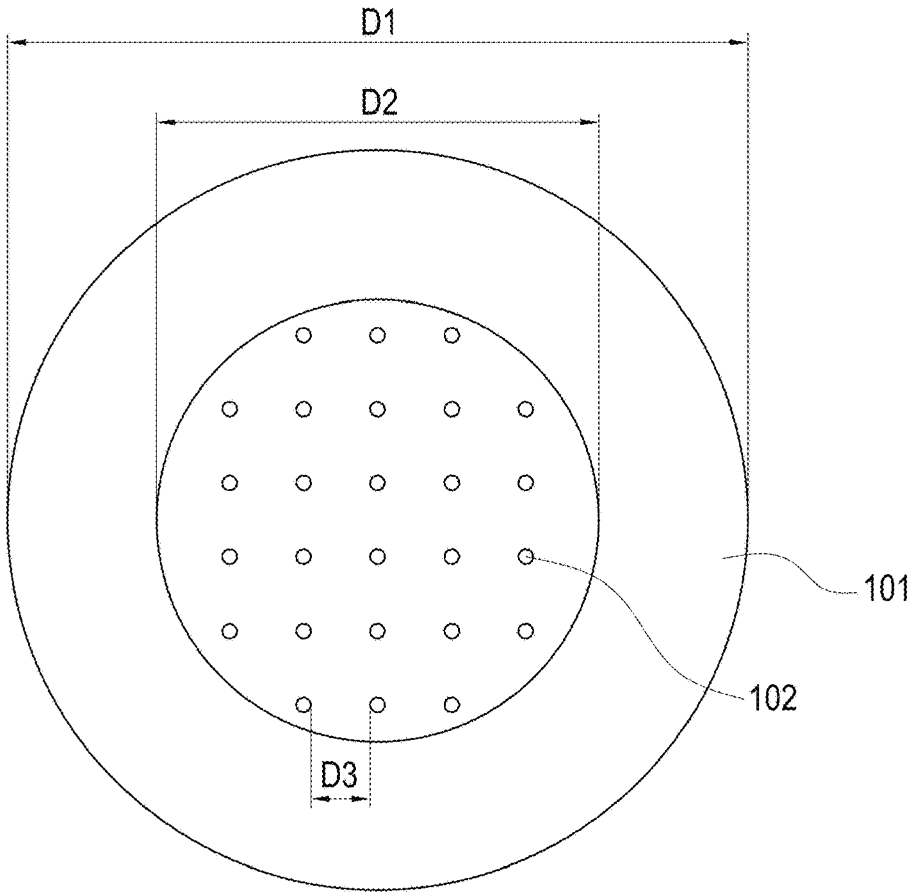
FIG. 5 is the enlarged top view of the nano channel holes mapped to one cell cavity.

FIG. 4A is the top view of the MEMS nano channel plate 100. FIG. 4B is the side view of the MEMS nano channel plate 100. FIG. 5 is the enlarged top view of the nano channel holes 102 mapped to one cell cavity 301. The MEMS nano channel plate 100 is made of silicon wafer through inductively coupled plasma (ICP) process. The thickness H1 of the MEMS nano channel plate 100 is about 200 um to 650 um, and 400 um is more desirable. Inside the MEMS nano channel plate 100, each well 101 is mapped to each cavity 301 (cell cavity). As shown in FIG. 5, multiple nano channel holes 102 are defined with a spacing D3 between 5 um to 15 um, and 5 um is more desirable. A dead area zone is defined between the distance D1 to the distance D2. The dead area zone may increase mechanical strength for the thin area within the distance D1. In the area within the distance D1, the thickness H2 of the MEMS nano channel plate 100 is between 7.5 um to 20 um. The thickness H2 is limited by the size of the nano channel hole 102. The diameter of the nano channel hole is set to be between 0.5 um to 1 um, and 1 um is more desirable.

Figure 6:
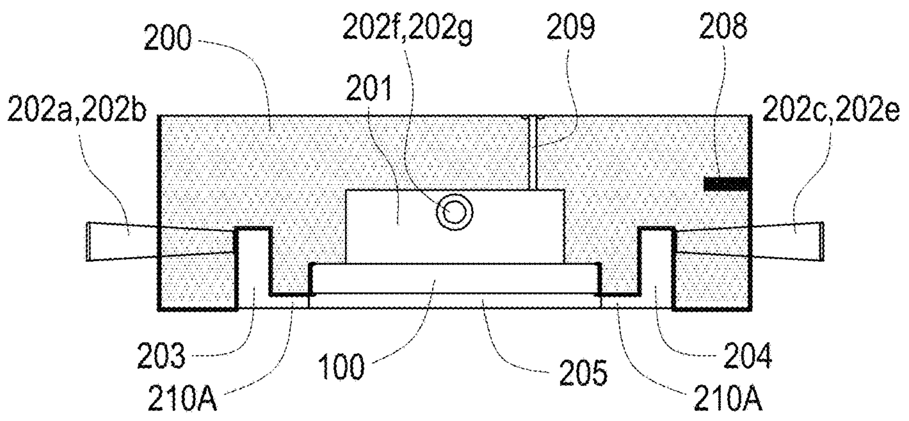
FIG. 6 is the schematic diagram of the MEMS cap and the MEMS nano channel plate.

FIG. 6 is the schematic diagram of the MEMS cap 200 and the MEMS nano channel plate 100. The inlets 202*a*, 202*b* are the inlets for the cell solution and washing solution respectively. The input buffer area 203 is connected with the inlets 202*a*, 202*b*. The outlets 202*c*, 202*d*, 202*e* are disposed opposite to the inlets 202*a*, 202*b*. The output buffer area 204 is connected with the outlets 202*c*, 202*d*, 202*e*. The cell EP chamber 205 has a height of 100 um to 300 um. The fluid flow through the input buffer area 203, the cell EP chamber 205, and the output buffer area 204 by the narrow gap area 210A. The gap G (as shown in FIG. 3) between the MEMS nano channel plate 100 and the cell cavity plate 300 is defined from the top surface of the cell cavity plate 300 to the bottom of MEMS nano channel plate 100, and the gap G of 100 um is more desirable. The bottom of the MEMS cap 200 is attached to the cell cavity plate 300 with an adhesive in the surrounding for sealing.

As shown in FIG. 6, the MEMS nano channel plate 100 is attached (or glued) to the MEMS cap 200 with a conductive adhesive. The MEMS nano channel plate 100 is connected to the external terminal pole 208 through the metal layer 207. During EP phase, the external terminal pole 208 is connected to the negative terminal of the voltage source from the EP controller 900. On the top of the MEMS nano channel plate 100, the exogenous material chamber 201 is defined between the top of MEMS nano channel plate 100 and the MEMS cap 200 with the inlet 202*f* and the outlet 202*g*. The exit hole 209 may be optionally defined on the top surface of the MEMS cap 200, which communicates the exogenous material chamber 201 with outside for air exit during filling of exogenous material through inlet 202*f*.

Figure 7:
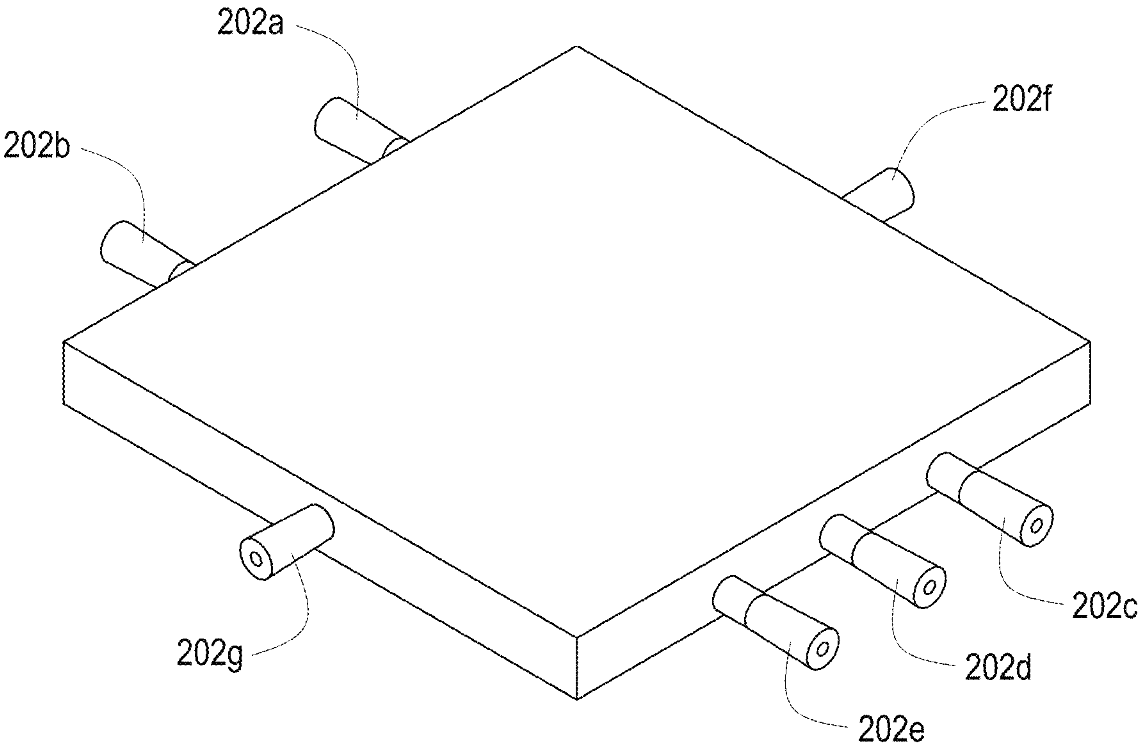
FIG. 7 is the 3D view of the MEMS cap with inlets and outlets.

FIG. 7 is the 3D view of the MEMS cap 200 with the inlets 202*a*, 202*b*, 202*f* and the outlets 202*c*, 202*d*, 202*e*, 202*g*. The MEMS cap 200 is molded with bio-compatible plastics, such as polycarbonate (PC), or polymethyl methacrylate (PMMA) etc.

One embodiment of present invention to use the inlets 202*a*, 202*b*, 202*f* and the outlets 202*c*, 202*d*, 202*e*, 202*g* is described below. The inlet 202*a* is used for inputting the cell solution, the inlet 202*b* is used of inputting the washing solution (for example, Phosphate Buffered Saline (PBS)), the outlet 202*c* is used for outputting the cell solution, the outlet 202*d* is used for outputting the washing solution, the outlet 202*e* is used for outputting the transfected cell, the inlet 202*f* is used for inputting the exogenous material solution, and the outlet 202*g* is used for outputting the exogenous material solution, here is not intended to be limiting.

One embodiment of the operation steps of present invention is as below.

Step 1: Activating syringe pump assembly to open the inlet 202*a* and the outlet 202*c* for the cell solution to flow into the cell EP chamber.

Step 2: Waiting a predetermined time period (for example, 1 min to 10 mins) for the cells to drop into the cell cavity by gravity.

Step 3: Applying the washing solution from the inlet 202*b* and collecting extra cells from outlet 202*c*, which are not falling into the cavities.

Step 4: Filling the exogenous material solution through the inlet 202*f*.

Step 5: Applying EP voltage pulses.

Step 6: Using ultrasound vibration to pop out the cells from the cavities, and then applying the washing solution from the inlet 202*b* and collecting the electroporated cells from the outlet 202*e*.

Step 7: Repeating step 1 to step 7 except step 4 for next batch operation until the end of the cells and/or the exogenous material solution. In other words, the EP operation is continuously operated in batch.

Referring back to FIG. 1, During EP phase, the EP controller 900 is triggered by the system controller 700 to generate voltage pulses with predefined amplitude, ON/OFF time period and pulse number. The ON time period may be from 1 ms to 20 ms, the OFF time period may be from 1 sec to 100 sec, and the pulse number may be from 1 to 20 depending on cell type and exogenous material for dose control. The EP voltage may be varied from 10 V to 90 V, the range between 10 V to 30 V is more desirable.

After the EP phase is finished, the system controller 700 activates the ultrasound vibrator (cell pop up device 600) with amplitude, duty cycle and duration control to pop up cells from cavities and then move out cells from the cell EP chamber 205 by inputting the washing solution from the inlet 202*b* and collecting the transfected cells from the outlet 202*e*. The input and output operation control is done by the syringe pump assembly 800 (with controller), the controller of the syringe pump assembly 800 may control up to 8 syringe pumps simultaneously. Each inlet or outlet is controlled by one syringe pump that the fed speed and duration time may be controlled by the controller of the syringe pump assembly 800.

The ultrasound vibrator (cell pop up device 600) may be made of a piezoelectric device with a material such as polyvinylidene fluoride (PVDF) or lead zirconate titanate (PZT) etc., and the material of PZT is more desirable. The ultrasound frequency of the ultrasound vibrator is between 20 Khz to 200 Khz, and 40 khz is more desirable.

Figure 8A:
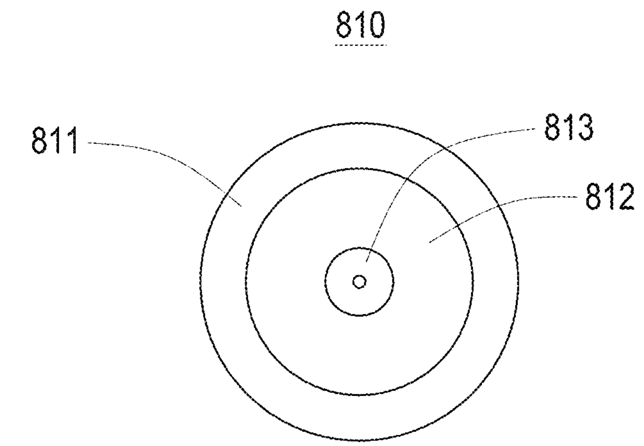
FIG. 8A is the top view of the needle adaptor.
Figure 8B:
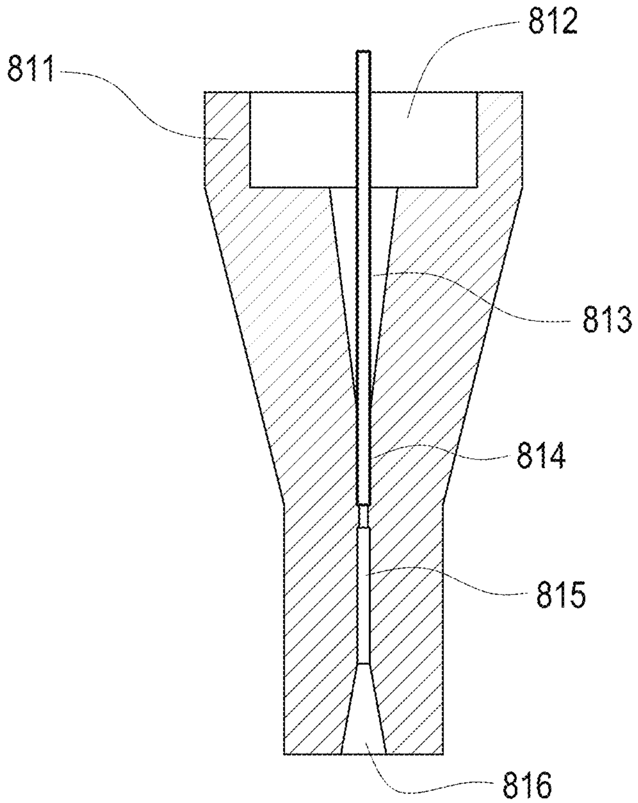
FIG. 8B is the side view of the needle adaptor to be connected to syringe needle for inputting or outputting solution mixture.

The connection between the inlets 202*a*, 202*b*, 202*f* the outlets 202*c*, 202*d*, 202*e*, 202*g* and the syringe pump assembly 800 is using the plastic tube (for example, polyethylene (PE) tube). The insertion of the plastic tube to the MEMS cap 200 is fixed by adhesive, and another side of the plastic tube is connected to a needle adaptor 810 as shown in FIG. 8A and FIG. 8B. FIG. 8A is the top view of the needle adaptor. FIG. 8B is the side view of the needle adaptor to be connected to syringe needle for inputting or outputting solution mixture. One silicone cap 812 is inserted on the top of the needle adaptor housing 811 having the guide hole 813. At the end of the needle guide hole 813 is the needle fixture area 814. On the other side of needle adaptor housing 811 is a plastic tube guide hole 816 with an end section 815 of tube fixture. The plastic tube is fixed to the needle adaptor housing 811 by adhesive.

Figure 9A:
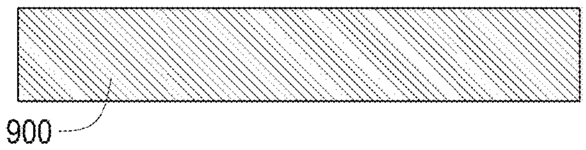
FIG. 9A to FIG. 9H are the schematic diagram of the fabrication process for the MEMS nano channel plate.
Figure 9E:
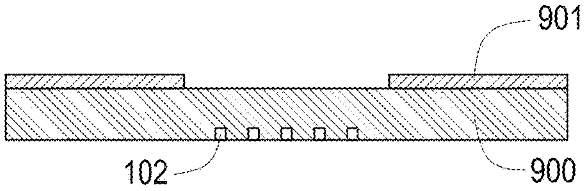
Figure 9B:
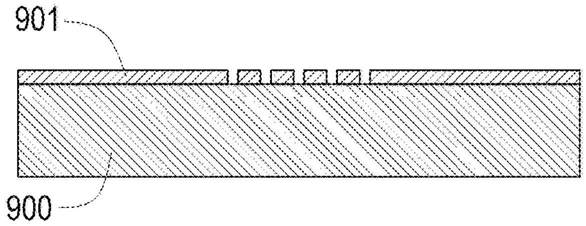
Figure 9F:
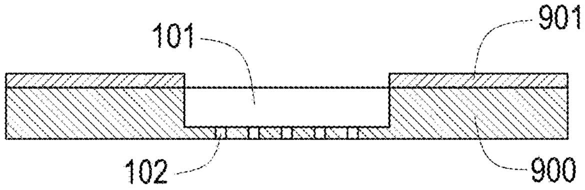
Figure 9C:
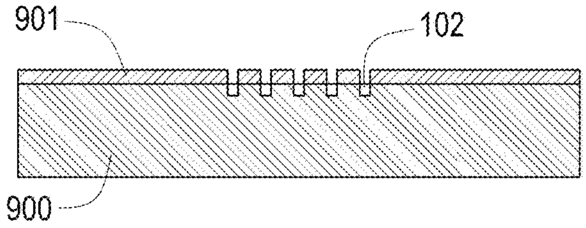
Figure 9G:
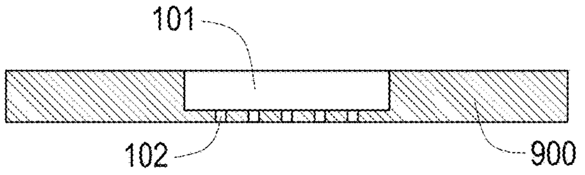
Figure 9D:
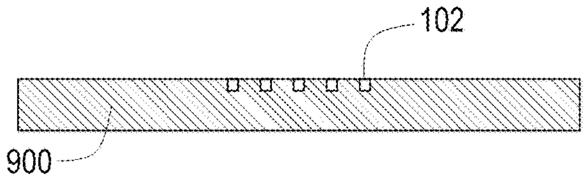
Figure 9H:
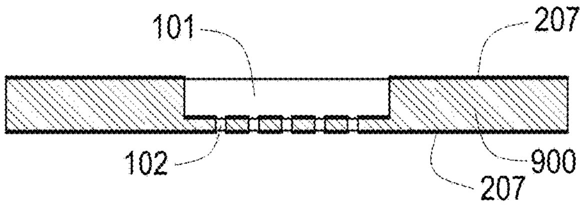

FIG. 9A to FIG. 9H are the schematic diagram of the fabrication process for the MEMS nano channel plate. It should be noted that the drawings only depict one well with multiple nano channel holes, which is mapped to one cell cavity. As shown in FIG. 9A, the step S11 is providing the silicon wafer 900. As shown in FIG. 9B, the step S12 is patterning with the metal mask 901 for the locations of the nano channel holes. As shown in FIG. 9C, the step S13 is forming the nano channel holes 102 by dry etching, such as ICP. As shown in FIG. 9D, the step S14 is removing protection layer and thinning down the wafer 900 (for example, the thickness of 300 um to 650 um, and 400 um is more desirable). As shown in FIG. 9E, the step S15 is flipping the wafer 900 upside down and patterning area for the well 101, which is mapped to one cell cavity. As shown in FIG. 9F, the step S16 is using deep reactive ion etching (RIE) to make the nano channel holes 102 be exposed in the well 101. For example, if the diameter of the nano channel hole 102 is 1 um and depth of the nano channel hole is 15 um, the well 101 needs to be etched at least 385 um when the wafer thickness is 400 um. As shown in FIG. 9G, in step S17, the protection layer is removed. As shown in FIG. 9H, in step S18, the MEMS nano channel plate 100 is coated with bio-compatible metal layer 207 (for example, gold layer) on both sides. Alternatively, the bio-compatible metal layer 207 being coated in the step S18 may be one side only.

Figure 10A:
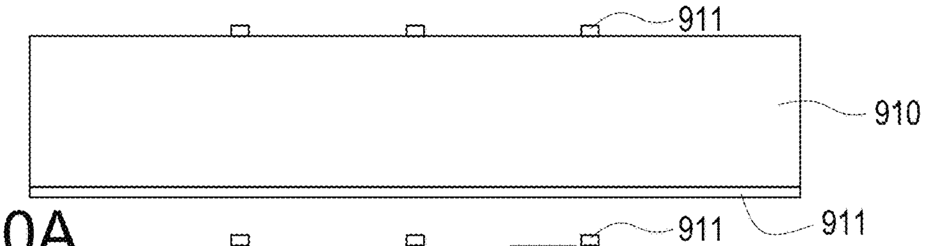
FIG. 10A to FIG. 10G are the schematic diagram of the fabrication process for the cell cavity plate.
Figure 10B:
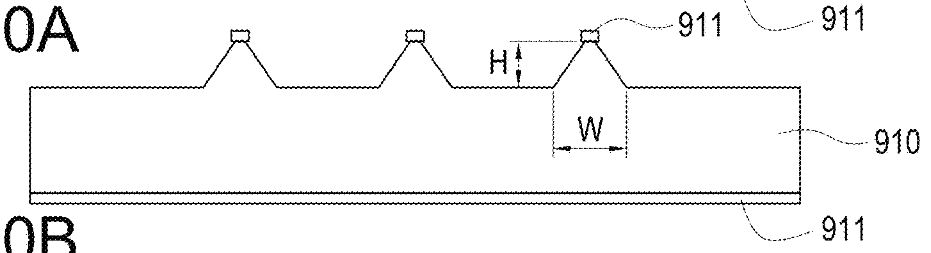
Figure 10C:
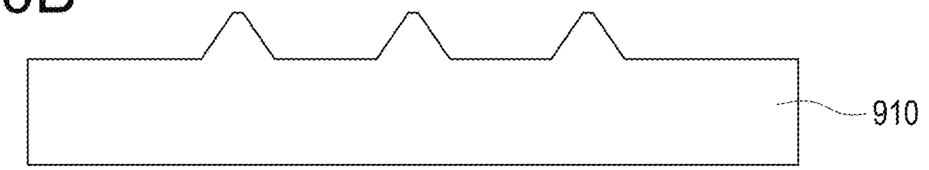
Figure 10D:
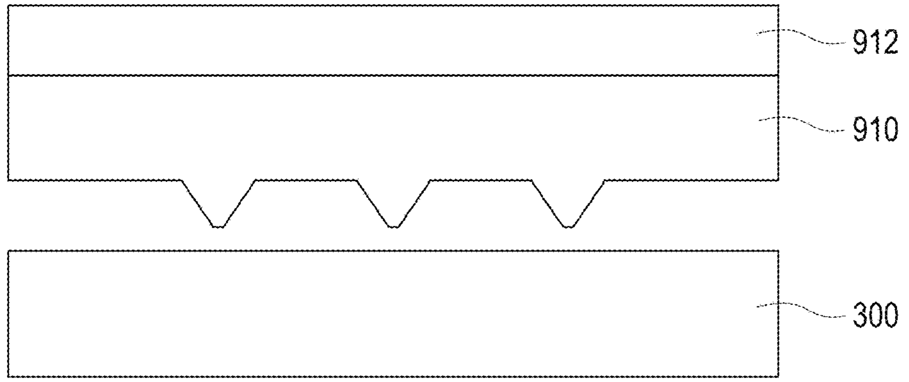
Figure 10E:
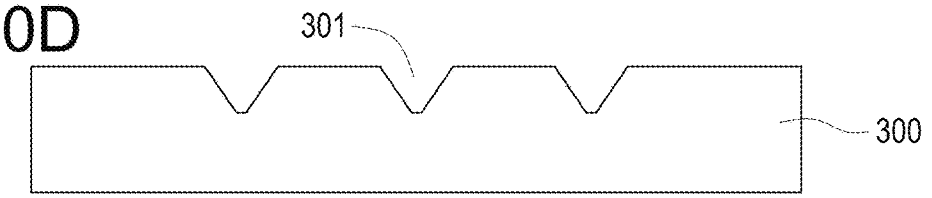
Figure 10F:
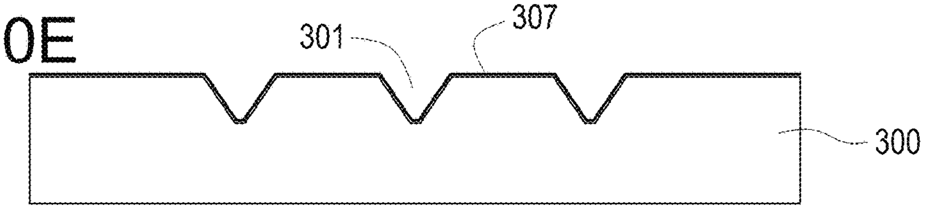
Figure 10G:
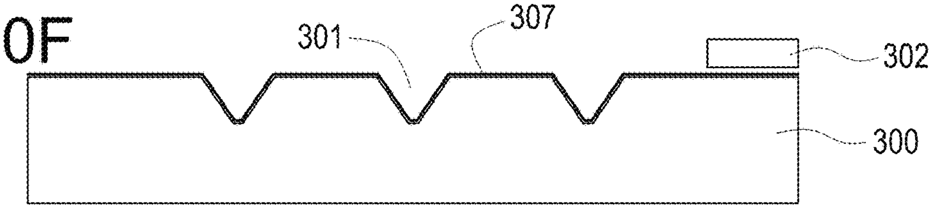

FIG. 10A to FIG. 10G are the schematic diagram of the fabrication process for the cell cavity plate 300. The cell cavity plate 300 is precision mold injected plastic part made of polycarbonate (PC) or PMMA. As shown in FIG. 10A, the step S31 is to pattern the protection layer 911 on the silicon wafer (silicon mold) 910 for wet etching. As shown in FIG. 10B, the step S32 is using anisotropic wet etching to etch down the silicon wafer 910 to form a hill shape with the height H of about 30 um and the width W of about 43 um. As shown in FIG. 10C, the step S33 is to remove the protection layer on both side of silicon wafer 910, and the silicon wafer 910 is used as a mold for subsequent hot stamping. As shown in FIG. 10D, the step S34 is flipping the silicon wafer 910 and attaching the silicon wafer 910 to a heater 912 for hot stamping the cell cavity plate 300. The hot stamping temperature needs to exceed the glass transition temperature of plastic material of the cell cavity plate 300. As shown in FIG. 10E, the step S35 is forming the cavities 301 on the cell cavity formed plate 300. For a cell size of 20 um in diameter, the width W of the cavity 301 is about 43 um and the depth H of the cavity 301 is about 30 um. The size of the cavity 301 may hold one cell with the size of 20 um in diameter. As shown in FIG. 10F, the step S36 is to dispose thin bio-compatible metal layer 307 (for example, gold layer) on top surface of the cell cavity plate 300. For visibility of the cell inside the cavity 301, the coated metal layer 307 needs to be thin, such as in the nano meter range (for example, less than 50 nm). As shown in FIG. 1, the adaptor 500 for the main EP chamber assembly 2 has center opening that provides visibility of cell inside the cavity through inverted microscope. As shown in FIG. 10G, the step S37 is printing the electrical connection terminal 302, such as conductive adhesive, on top edge of cell cavity plate 300.

Figure 11:
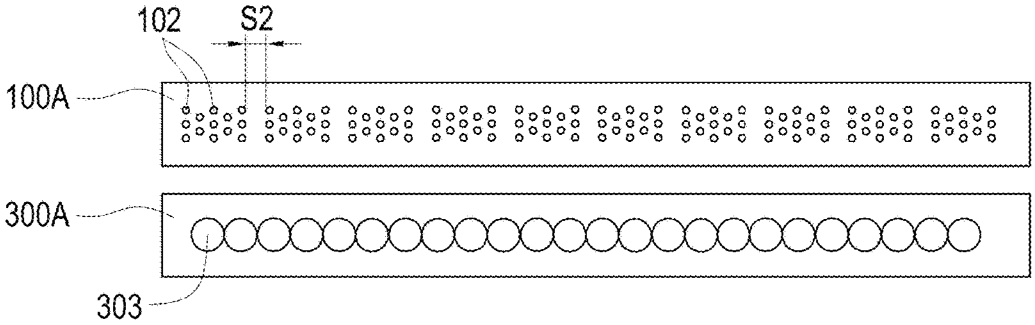
FIG. 11 is the schematic diagram of another embodiment of the MEMS nano channel plate and the cell cavity plate in a striped-type.

FIG. 11 is the schematic diagram of another embodiment of the MEMS nano channel plate 100A and the cell cavity plate 300A in a striped-type. Another embodiment of the microfluidic EP device is to use the MEMS nano channel plate 100A and the cell cavity plate 300A in a striped-type to increase the transfection cell number per unit area. In FIG. 11, the MEMS nano channel plate 100A has the nano channel holes 102 in group, and the groups are spaced with a distance S2. The spacing is used to increase the mechanical strength of the MEMS nano channel plate 100A. The distance S2 may be less than cell size (for example, 10 um). The cell cavity plate 300A is filled with the cell 303 lining up in a striped form. The cavity of the cell cavity plate 300A may be rectangular shape or V-grooved shape. Both the MEMS nano channel plate 100A and the cell cavity plate 300A may have multiples stripes, which are aligned with each other in vertical direction. For the stripe type design of the MEMS nano channel plate 100A and the cell cavity plate 300A, the EP parameters are the same as the design of single cavity per cell.

Figure 12:
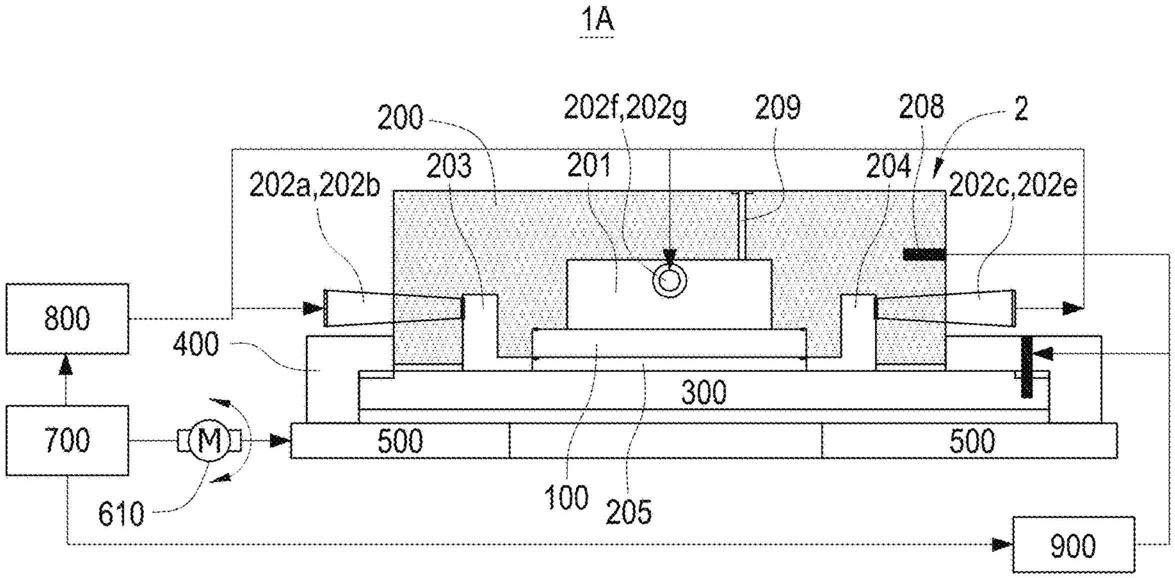
FIG. 12 is the schematic diagram of another embodiment of a microfluidic EP device with a motorized rotator for popping out cells from cavities after EP.

FIG. 12 is the schematic diagram of another embodiment of a microfluidic EP device 1A with a motorized rotator 610 for popping out cells after EP. The cell pop up device is a motorized rotator 610 to flip the EP chamber assembly 2 upside down (that is, 180 degrees) after EP phase is finished. The upside down operation is used to pop up the cells from the cavities, and then a washing solution is applied from the inlet 202*b* to get the transfected cells out from the outlet 202*e*. The design may improve cell viability without using ultrasound vibration.

Therefore, compared with the related art, the present invention provides high speed, high viability, and high efficiency transfection of exogenous molecules into cells. The present invention uses the nano channel holes for exogenous molecules (which is negative charged) to pass through, while the cells to be transfected on the cavities are connected to positive voltage during EP phase. A group of holes of the MEMS nano channel plate is mapped to one cavity of the cavity plate on bottom with narrow gap such as 100 um to 300 um. An ultrasound vibrator or a motorized rotator may be used to pop up cells from cavities, and then the washing solution is used to collect the transfected cells from the outlet. The whole EP operation is controlled by the system controller, that the EP operation may be executed continuously in batch. The disclosed microfluidic EP device is capable of transfecting multiple cells simultaneously, which has high viability and high efficiency.

The above is only a detailed description and drawings of some embodiments of the present invention, but the features of the present invention are not limited thereto, and are not intended to limit the present invention. All the scope of the present invention shall be subjected to the scope of the following claims. The embodiments of the spirit of the present invention and its similar variations are intended to be included in the scope of the present invention. Any variation or modification that may be easily conceived by those skilled in the art and in the field of the present invention may be covered by the following claims.

What is claimed is:

1. A microfluidic electroporation (EP) device, comprising:

an EP chamber assembly, comprising:

a MEMS nano channel plate, comprising multiple nano channel holes, an exogenous material passing through the nano channel holes for a cell EP operation;

a MEMS cap, disposed above and attached to the MEMS channel plate, comprising multiple inlets and multiple outlets, and an exogenous material chamber defined between the MEMS cap and the MEMS nano channel plate;

a cell cavity plate, disposed below and attached to the MEMS cap by an adhesive sealing, comprising multiple cavities to hold multiple cells, the cavities vertically aligned with the nano channel holes, and a cell EP chamber defined between the cell cavity plate and the MEMS nano channel plate;

a first electrode, disposed on the MEMS nano channel plate;

a second electrode, disposed on the cell cavity plate; and a cell cavity plate holder, connected with the MEMS cap and the cell cavity plate;

an adaptor, connected with the EP chamber assembly;

a cell removal device, connected with the adaptor;

a syringe pump assembly, connected with the inlets of the MEMS cap through multiple first tubes to input a cell solution, a washing solution, or an exogenous material solution, and connected with the outlets of the MEMS cap through multiple second tubes to output the cell solution, the washing solution, transfected cell solution or the exogenous material solution;

an EP controller, configured to generate multiple EP voltage pulses with an ON/OFF period, a pulse number, and a voltage level control, wherein the EP controller comprises a negative terminal and a positive terminal, the negative terminal is connected to the first electrode, and the positive terminal is connected to the second electrode; and a system controller, electrically connected to the syringe pump assembly, the EP controller, and the cell removal device, and configured to control a sequence of multiple cell EP operations, wherein, the cell removal device is configured to remove the cells from the cavities after the cell EP operations, and the cells are outputted and collected from one of the outlets of the MEMS cap.

2. The microfluidic EP device of claim 1, wherein the cell removal device is an ultrasound vibrator or a motorized rotator.

3. The microfluidic EP device of claim 2, wherein an amplitude, an ON/OFF period and a duration of the ultrasound vibrator are controllable.

4. The microfluidic EP device of claim 3, wherein the ultrasound vibrator is made of a material of a polyvinylidene fluoride (PVDF) or a lead zirconate titanate (PZT).

5. The microfluidic EP device of claim 3, wherein a frequency of ultrasound vibrator is equal to or greater than 20 Khz and equal to or less than 200 Khz.

6. The microfluidic EP device of claim 5, wherein the frequency of ultrasound vibrator is 40 Khz.

7. The microfluidic EP device of claim 2, wherein the motorized rotator is configured to rotate the EP chamber assembly by 180 degrees to collect the cells after the cell EP operations.

8. The microfluidic EP device of claim 1, wherein the MEMS nano channel plate is made of a silicon wafer, and a thickness of the MEMS nano channel plate is equal to or greater than 300 um and equal to or less than 650 um.

9. The microfluidic EP device of claim 8, wherein the thickness of the MEMS nano channel plate is 400 um.

10. The microfluidic EP device of claim 1, wherein each MEMS nano channel hole comprises a diameter of equal to or greater than 0.5 um and equal to or less than 1 um.

11. The microfluidic EP device of claim 1, wherein the cell EP chamber comprises a height of equal to or greater than 100 um and equal to or less than 300 um.

12. The microfluidic EP device of claim 1, wherein each EP voltage pulse is equal to or greater than 10V and equal to or less than 90V.

13. The microfluidic EP device of claim 1, wherein a gold layer is coated on the cell cavity plate.

14. The microfluidic EP device of claim 13, wherein a thickness of the gold layer is equal to or less than 50 nm.

15. The microfluidic EP device of claim 1, wherein the cavities of the cell cavity plate are in a striped-type, and each cavity is of a rectangular shape or a V-grooved shape.

16. The microfluidic EP device of claim 15, wherein the nano channel holes of the MEMS nano channel plate are in a striped-type, and the nano channel holes are aligned with the cavities in the striped-type.

17. The microfluidic EP device of claim 1, wherein the first tube and the second tube respectively comprise a needle adaptor connected to a needle of the syringe pump assembly.

18. The microfluidic EP device of claim 1, wherein the cell cavity plate is made of a polycarbonate or a PMMA.

19. The microfluidic EP device of claim 1, wherein the MEMS cap comprises an exit hole connected to the exogenous material chamber.

* * * * *